US011259731B2

(12) United States Patent
Venditti et al.

(10) Patent No.: US 11,259,731 B2
(45) Date of Patent: Mar. 1, 2022

(54) TELEMETRY INTEGRATED SYSTEM

(71) Applicant: Formula Center Italia S.R.L., Larino (IT)

(72) Inventors: Davide Venditti, Larino (IT); Gaetano Venditti, Larino (IT)

(73) Assignee: FORMULA CENTER ITALIA S.R.L., Campobasso (IT)

( * ) Notice: Subject to any disclaimer, the term of this patent is extended or adjusted under 35 U.S.C. 154(b) by 0 days.

(21) Appl. No.: 16/971,121

(22) PCT Filed: Mar. 7, 2019

(86) PCT No.: PCT/IB2019/051841
§ 371 (c)(1),
(2) Date: Aug. 19, 2020

(87) PCT Pub. No.: WO2019/171314
PCT Pub. Date: Sep. 12, 2019

(65) Prior Publication Data
US 2021/0093242 A1    Apr. 1, 2021

(30) Foreign Application Priority Data
Mar. 9, 2018  (IT) .................. 102017000132925

(51) Int. Cl.
| G08B 23/00 | (2006.01) |
| A61B 5/18  | (2006.01) |
| A61B 5/00  | (2006.01) |
| A61B 5/024 | (2006.01) |
| A61B 5/0533 | (2021.01) |

(Continued)

(52) U.S. Cl.
CPC .............. *A61B 5/18* (2013.01); *A61B 5/0006* (2013.01); *A61B 5/02416* (2013.01); *A61B 5/0533* (2013.01); *A61B 5/0816* (2013.01); *A61B 5/1112* (2013.01); *A61B 5/6805* (2013.01); *A61B 5/6806* (2013.01); *B60W 40/08* (2013.01); *B60W 2040/0872* (2013.01); *B60W 2540/22* (2013.01); *B60W 2540/221* (2020.02)

(58) Field of Classification Search
CPC ..... A61B 5/18; A61B 5/0006; A61B 5/02416; A61B 5/0533; A61B 5/0816; A61B 5/1112; A61B 5/6805; A61B 5/6806; B60W 40/08; B60W 2540/221; B60W 2040/0872; B60W 2540/22
USPC ........................................................ 340/576
See application file for complete search history.

(56) References Cited

U.S. PATENT DOCUMENTS

| 6,016,103 A * | 1/2000 | Leavitt ................... G08B 21/06 340/575 |
| 2007/0028370 A1 * | 2/2007 | Seng ...................... A42B 3/046 2/410 |

(Continued)

*Primary Examiner* — Naomi J Small
(74) *Attorney, Agent, or Firm* — Mark Malek; Widerman Malek, PL

(57) ABSTRACT

A system for the integrated/functional detection of different measurements is described. The system comprises a part wearable by a driver of a vehicle and plurality of sensors integrated in the wearable part and configured to supply the following driver parameters: breathing parameters, heart parameters, perspiration parameters and of the pressure exerted on the vehicle driving wheel. The system also includes a processor for processing the driver parameters and correlating them to a driver psychophysical condition.

9 Claims, 5 Drawing Sheets

(51) Int. Cl.
*A61B 5/08* (2006.01)
*A61B 5/11* (2006.01)
*B60W 40/08* (2012.01)

(56) References Cited

U.S. PATENT DOCUMENTS

| | | | | |
|---|---|---|---|---|
| 2009/0150965 | A1* | 6/2009 | Christianen | A63B 24/0021 |
| | | | | 725/135 |
| 2010/0106365 | A1* | 4/2010 | Visconti | B60H 1/00742 |
| | | | | 701/36 |
| 2012/0319847 | A1* | 12/2012 | Heller | A61B 5/0022 |
| | | | | 340/573.1 |
| 2013/0325202 | A1* | 12/2013 | Howard | B60W 40/09 |
| | | | | 701/1 |
| 2015/0355311 | A1* | 12/2015 | O'Hagan | H04W 4/029 |
| | | | | 340/539.13 |
| 2017/0136842 | A1* | 5/2017 | Anderson | A61B 5/4023 |
| 2017/0153636 | A1* | 6/2017 | Boesen | G06F 1/163 |
| 2018/0082501 | A1* | 3/2018 | Kochhar | G06F 1/163 |
| 2018/0133583 | A1* | 5/2018 | Tran | A63B 24/0075 |
| 2018/0289166 | A1* | 10/2018 | Andon | A61B 5/6823 |
| 2019/0147711 | A1* | 5/2019 | Grom | G08B 5/36 |
| | | | | 340/539.13 |
| 2020/0253294 | A1* | 8/2020 | Van de Zande | G06F 3/011 |

* cited by examiner

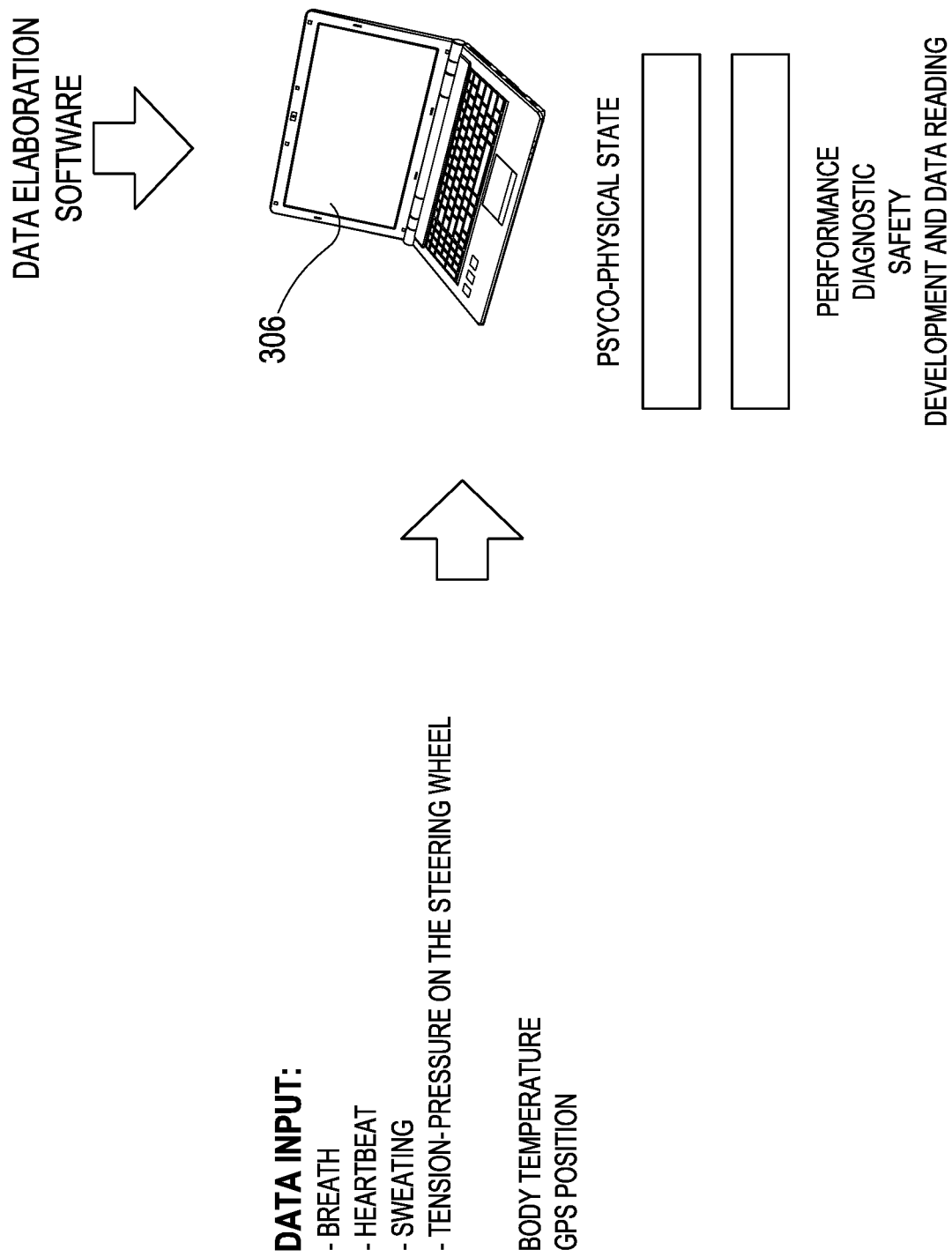

TELEMETRY INTEGRATED SYSTEM

RELATED APPLICATIONS

This application is a national phase application of and claims priority under 35 U.S.C. § 371 of PCT Application No. PCT/IB2019/051841 filed on Mar. 7, 2019 and titled TELEMETRY INTEGRATED SYSTEM. The content of this application is incorporated herein by reference.

TECHNICAL BACKGROUND OF THE INVENTION

The present invention refers to the field of the human telemetry.

PRIOR ART

The human telemetry, in the context of sport competitions, is a relatively new discipline, grown in the more general field for remotely measuring physical magnitudes regarding human activities. Particularly, with reference to car racing, it is related to the way of acquiring, storing, and remotely transmitting biomechanical parameters of a driver, which can be related to his/her psychophysical condition, in order to obtain useful information regarding his/her behavior, diagnostics, and safety.

Katsis C. D. et al. in "Toward Emotion recognition in Car-Racing Drivers: biosignal Processing approach", IEE Transactions on Systems, Man and Cybernetics. Part A: Systems and Humans, IEEE Service Center, Piscataway, N.J., U.S., vol. 38, no. 3; Jan. 5, 2008, pages 502-512, XP011226354, describes a system for estimating an emotional condition of a driver in a car race.

Document EP-A-3015055 describes a system for monitoring psychological parameters of a vehicle driver.

The Applicant has observed that the known type human telemetry systems applied to vehicle drivers are not satisfying in determining the psychophysical condition of the driver.

SUMMARY OF THE INVENTION

The object of this invention consists of providing an improved "wearable" human telemetry system overcoming the disadvantages of the prior art.

The invention can be applied to the automotive field from the racing to the safety areas.

One of the main uses of the system consists of monitoring the physical parameters of a motorsport driver when he/she trains or races. A further application in the safety optics of the system could be related to a widespread use of such system in the driver training centers.

Moreover, the invention comprises, according to an example, an analytical-numerical study about the obtained experimental results, useful to correlate the acquired data by wearable sensors to the data from the inboard standard telemetry. Based on such study, it will be possible to optimize the driver behavior under different driving conditions and to better estimate the racing strategies, by considering both the present conditions of the driver and the mechanical performance of the vehicle.

By a preliminary analysis about the driver parameters which are more related to his/her psychophysical conditions, the following magnitudes to be sensed were selected: breathing rate, heart rate and ECG, electric impedance of the skin and perspiration, pressure on the driving wheel, as shown in FIG. 1. In addition, the position on the track is advantageously sensed by a GPS technique.

It is an object of the invention a system for the integrated/functional detection of a plurality of measurements as defined in claim 1 and by preferred embodiments thereof, defined in the dependent claims.

BRIEF DESCRIPTION OF THE FIGURES

The constructive and operative characteristics of the invention could be better understood from the following detailed description, in which it is made reference to the attached drawings representing some preferred non-limiting embodiments thereof, wherein:

FIG. 5 schematically shows the correlation processing of the detectable parameters.

DETAILED DESCRIPTION

The telemetry system (generally shown in FIGS. from 1 to 5) comprises a wearable part 200 having two parts formed by a underwear/(possibly fireproof) undershirt 201 and two gloves 202, suitably instrumented by miniaturized devices for not interfering with the normal activities of the driver.

Figure 1:
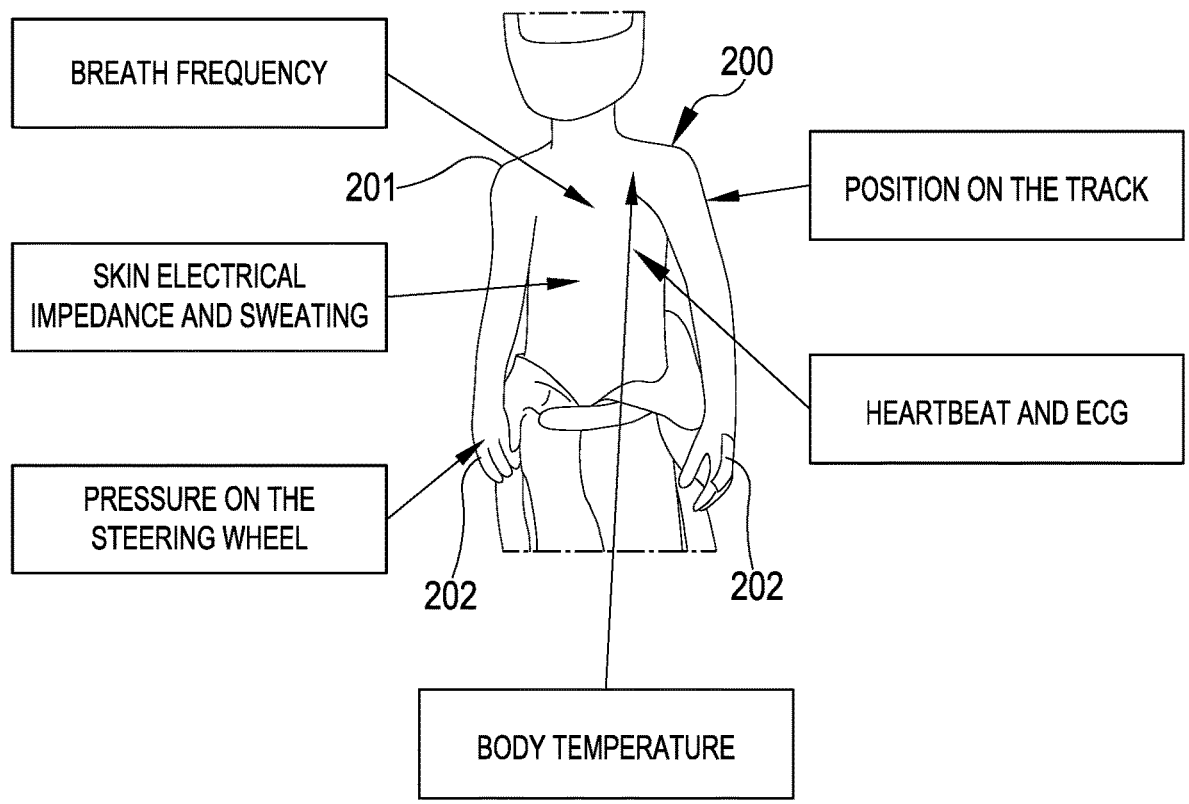
FIG. 1 illustratively shows the telemetry system according to the invention and shows the parameters obtainable by the system itself.
Figure 2:
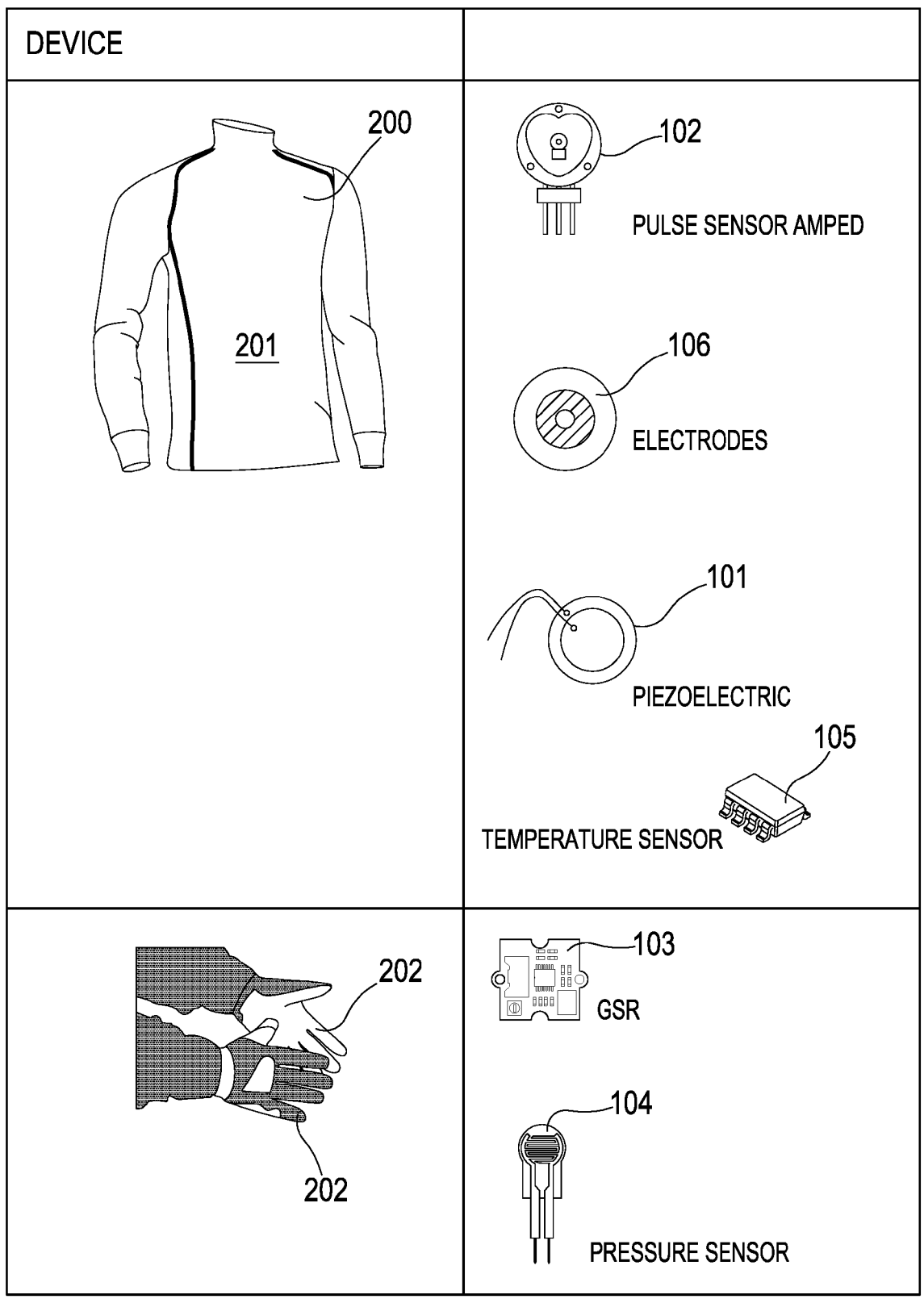
FIG. 2 illustratively shows a plurality of sensors used by the telemetry system.

Referring particularly to FIGS. 1 and 2, the selection of the sensors used for the telemetry systems is explained.

Breathing rate: measuring the number of breathing acts in a determined time range (breathing rate) is performed by piezoelectric wearable sensors 101, inserted in a thoracic band sewn in the internal part of the underwear 201.

Heart rate and ECG: the heart rate is measured by an optical heart beat sensor 102 (Pulse Sensor Amped), using the photoplethysmography technique (PPG) or similar. The sensor 102 must be placed in the body most vascularized parts. The ECG is sensed by using a sensor provided with textile electrodes 106, sewn inside the fireproof underwear 201, and tightly positioned against the driver breast.

It is observed that the breathing rate can be estimated by the heart rate.

Electric impedance of the skin and perspiration: sensing the electric impedance of the skin and perspiration is performed by measuring the Galvanic Skin Response (GSR) defined as a change of the electric properties of this latter due to events generating stress and/or perspiration. The small-sized sensor GSR 103 can be inserted in the cuffs of the driver underwear 201.

The Galvanic Skin Response (GSR), defined as one among several electrodermal responses, represents the measurement of continuous variations of the electric characteristics of the skin, e.g. the conductance, caused by a perspiration variation of the human body. The traditional assumption regarding the GSR analysis is based on the hypothesis that the skin resistance varies as a function of the skin sweat glands. The human body perspiration is adjusted by the Autonomous Nervous System (ANS); particularly, when the sympathetic branch (SNS) of the autonomous nervous system is highly energized, consequently the activity of the skin sweat glands increases, which in turn increases the skin conductance, and viceversa. So, the skin conductance can be a measure of the Sympathetic Nervous System responses. This system, in the human beings, is directly implied in the adjustment of the emotional behavior.

The human skin is a good electric conductor and when a low electric current is supplied to the skin, conductivity changes can be measured. The conductance is characterized by two components: tonic and phasic.

The tonic component is the cause of the slow variation of the GSR signal (from tenths of seconds to minutes). in a GSR signal, the tonic level is generally considered the background activity level, at the top of which rapid GSR responses appear. The tonic level represents the absolute value of the skin electric resistance and is an index of the general activation state of the nervous system of an organism. It is higher if a person is at rest, and relaxed, on the contrary if the person is tired and nervous, it increases the skin perspiration and lowers the skin electric resistance.

The phasic component is the cause of relatively rapid variations of the GSR signal (in the order of seconds) known as skin conductance responses and represent the rapid fluctuations or peaks which are observed in a GSR signal, caused by a purely emotional and sensory activity. According to the present description, at least the phasic component is provided.

Pressure exerted on the driving wheel: the grip on the driving wheel is detected by inserting inside the driver's gloves 202, on the hand palm and fingers, several pressure sensors 104 of the extensometric type, o similar.

Position in the track: the position of the car in a track is detected by a GPS module, having an acquisition frequency of at least 30 Hz, and inserted inside the suit or in the passenger compartment.

Body temperature: measuring the body temperature by wearable devices can be performed in many different ways. It is provided a digital temperature sensor 105, suitably fixed to the underwear 201 by a thermal shield against the external heat flows, which enables to obtain skin temperature measurements from voltage variations.

Moreover, according to an example, the system is configured to provide, besides an absolute magnitude of the perspiration, the integrated detection of the electrolysis and glycolysis, in order to gain an adapted determination of food integrations required for the activity object of the detection.

Particularly, the system can be provided with an apparatus for detecting and monitoring the glucose.

Wearable devices for measuring in a semi-continuous way the glucose concentration (Continuous Glucose Monitoring, CGM) are known. Particularly, the CGM devices are classified in mini-invasive devices and non-invasive devices (still under experimentation).

The mini-invasive devices now on the market use a small needle, usually inserted in the sub-cutaneous tissue, for measuring an electric current signal proportional to the glucose concentration available in the interstitial liquid. CGM sensors are for example marketed by Dexcom, Medtronic, Abbot, Senseonics.

It is observed that a physical activity, related to the use of skeletal muscles, requires an energy input greater than the one required to a human being at rest. However, it is required to distinguish among: an aerobic physical activity: an activity entailing repeated continuous movements with a medium-low contraction rate of the muscular fibers, such as for example in the long-distance races, anaerobic physical activity: a very intense activity, characterized by a high contraction rate of the muscle fibers, such as for example in the motorsport races.

In the aerobic physical activity, the blood glycemia levels do not change even though the energy consumption of the muscles can substantially increase.

In the anaerobic activity, there is the anaerobic glycolysis, in other words a fast energy production without oxygen, because the epinephrine has an important role. The result is a hypoglycemic effect, since the amount of glucose released to the muscle cells is increased and the amount released to the blood is correspondingly reduced. If the basal glycemia levels immediately before the race trials are too low, probably the driver will be possibly subjected to a hypoglycemic fit.

For example, in an experimental test, the glycemia level of a motorsport driver was recorded during a race trial. It was observed that the basal glucose level, during such recording, was already below the nominal value. Drinking a fruit juice before the race led to a glycemia increase sufficient to compensate the glucose concentration loss during the race, in this way a too low glycemia level was prevented.

It is also observed that measuring the glucose level is also correlated to an energy consumption in the presence of an anaerobic metabolism. Generally, the energy is provided by a fat-carbohydrates mixture. However, in an anaerobic sporting activity, it is triggered a process of producing energy as ATP (Adenosine Triphosphate) obtained by substantially using storage sugar (glycogen) which is mainly found in muscles and liver. This information and the heart rate enable to evaluate, by tables, the used energy substrate.

Figure 3:
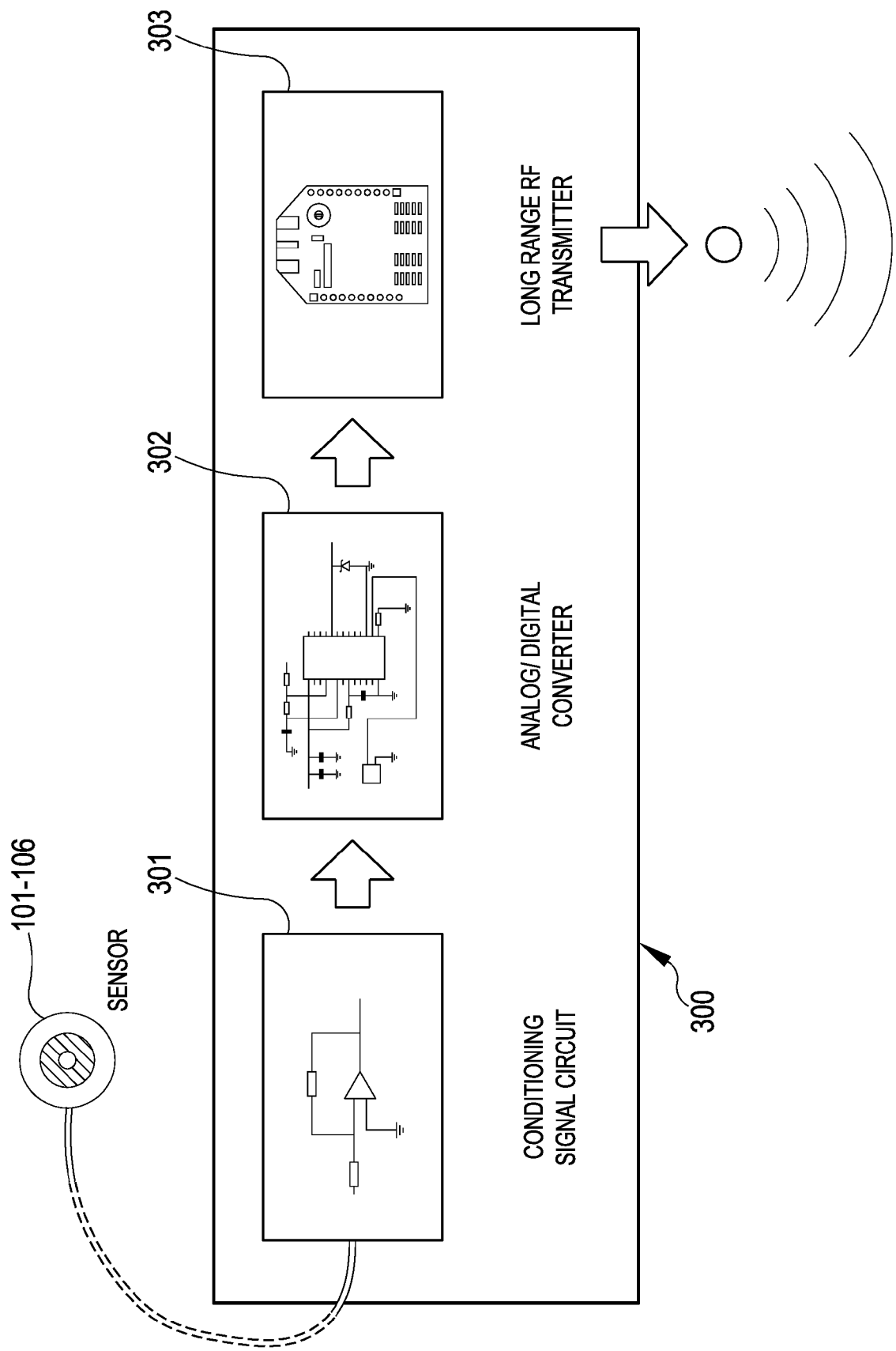
FIG. 3 illustratively shows a circuit for processing and transmitting signals from the sensors.
Figure 4:
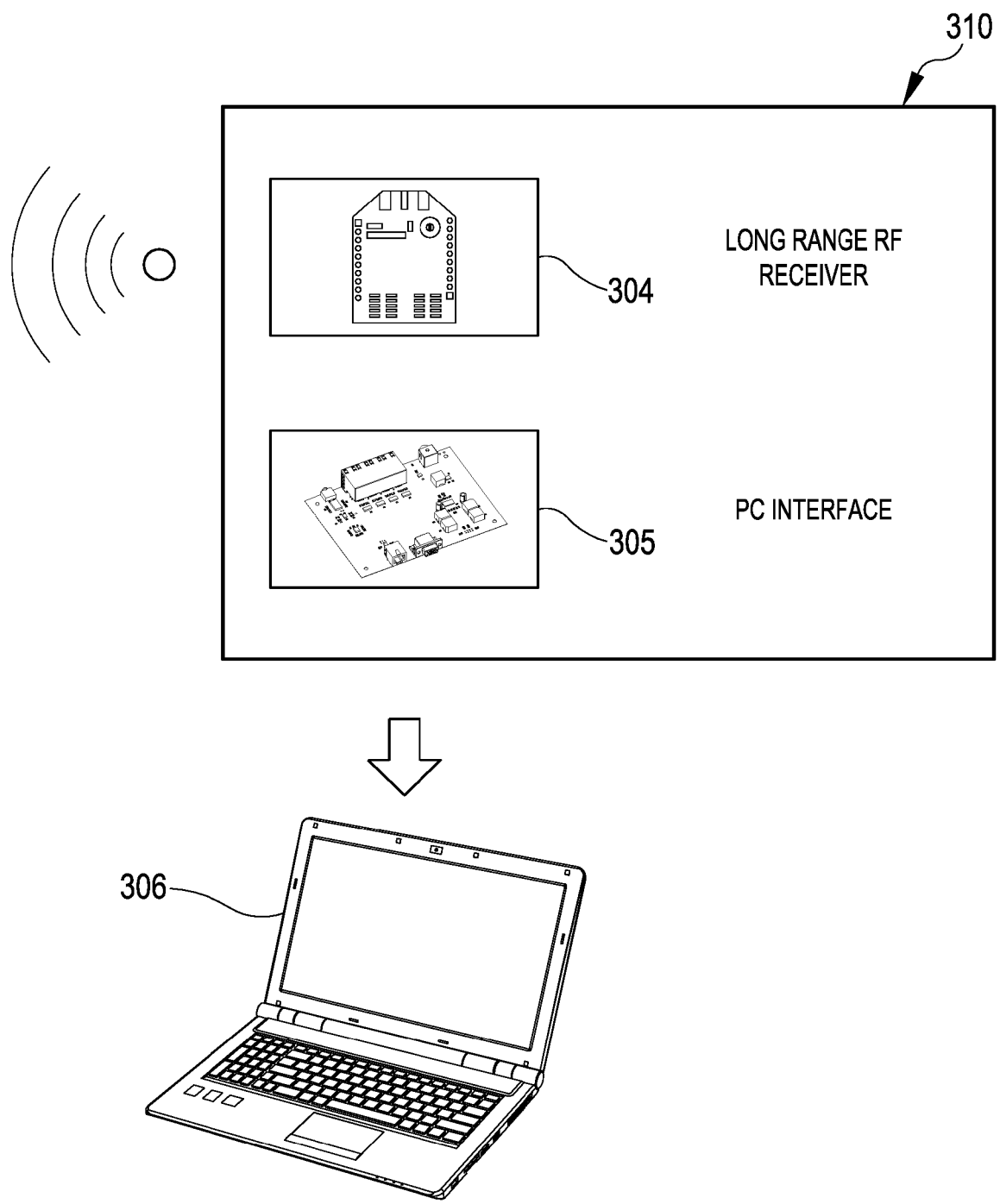
FIG. 4 illustratively shows a receiver and a Personal Computer adapted to receive the parameters transmitted by the processing and transmitting circuit.

With reference to FIG. 3, all the sensors 101-106 (and possibly the glucose sensor) are connected, by wire and/or wireless, to a pre-processing-transmission electronic card 300 comprising a signal conditioning module 301 and a converting module 302 performing an analog/digital conversion of the conditioned signals.

Moreover, the pre-processing-transmission electronic card 300 comprises a transmission module 303 (a radio frequency and long-distance, and/or a Bluetooth module) configured to transmit the sensor signals in a digital format outside the electronic card 300 itself. As an alternative to the transmission module 303 or in addition to it, the electronic card 300 can comprise or can be connected to a suitable storing device enabling to download data when the vehicle returns to the pits.

Advantageously, the system is connected to a suitable GPS for data positioning on the circuit.

The pre-processing-transmission electronic card 300 is for example placed inside a pocket made in the suit 201 and it such to deliver digital-format sensor data to a receiving-interface card 310 comprising a receiving module 304 (long-distance RF module, for example) and an interface card 305 with an electronic computer, such as for example a personal computer 306.

The transmitted signals are acquired by a radio-frequency receiving module 304 (connected to the personal computer 306).

The system comprises a screen-displaying software (FIG. 5) for showing the obtained data. A procedure of correlating performances to the psychophysical condition of the driver in different situations/states which can be occur in a driving session was developed from the method of acquiring human-inboard telemetry data (FIG. 5).

Particularly, it is possible to associate performances and driver psychophysical condition to the positions thereof along the path or circuit followed by the vehicle during the described parameter detection.

Particularly, the stress is evaluated by calculating a weighed average of at least the following parameters: a perspiration parameter, a heart parameter, a parameter regarding the pressure exerted on the driving wheel and, for example, also a breathing parameter. Advantageously, the stress is evaluated by taking into account into the above cited weighed average of a perspiration parameter representing the phasic component of the signal GSR, obtained from the signal provided by the sensor GSR 103. Moreover, such weighed average takes into account also the parameter regarding the glucose.

Lastly, batteries (e.g. rechargeable LiPo batteries) required for supplying the present sensors and devices are placed inside the suit 201 or car.

The invention claimed is:

1. A system for the integrated/functional detection of a plurality of measurements, the system comprising:
   a) a part wearable by a driver of a vehicle and provided with an undershirt/underwear and two gloves;
   b) a plurality of sensors integrated in the wearable part, and configured to supply the following plurality of driver parameters: breathing parameters, heart parameters, perspiration parameters and of the pressure exerted on the vehicle driving wheel;
   c) a pre-processing board mounted on said undershirt/underwear and comprising:
      a circuit connected to the plurality of sensors and configured to perform a conditioning of signals provided by said plurality of sensors producing a plurality of conditioned signals carrying said plurality of driver parameters;
      an analog/digital converter connected to the conditioning circuit and configured to convert the conditioned signals into a plurality of digital signals;
      a transmitter of long-distance radiofrequency (RF) connected to the analog/digital converter and configured to transmit the plurality of digital signals;
   d) a receiver of the long-distance radiofrequency (RF) for receiving the plurality of digital signals from the transmitter;
   e) a computer interface (305) connected to the receiver;
   f) a processor connected to said computer interface and configured to process said driver parameters and correlate said driver parameters to a psychophysical condition of the driver;
   wherein the processor is configured to calculate a driver stress index by processing said driver parameters according to a weighted average.

2. The system according to claim 1, wherein the plurality of sensors comprises:
   a breathing rate sensor inserted in a thoracic band sewn in an internal part of the underwear;
   a heart rate sensor defined by a heart rate optical type sensor that uses a photoplethysmography technique
   an ECG sensor with textile electrodes sewn inside the underwear.

3. The system according to claim 1, wherein the plurality of sensors comprises a sensor for detecting electric impedance of the skin and perspiration by measuring a galvanic response of the driver skin (GSR).

4. The system according to claim 1, wherein the plurality of sensors comprise a plurality of pressure sensors inserted inside said gloves on the palm and fingers of the driver hand.

5. The system according to claim 1, further comprising at least one digital-type body temperature sensor fixed to the underwear with a thermal shield against external heat flows to obtain measurements of skin temperature from voltage variations.

6. The system according to claim 1, further comprising a GPS module inserted inside or outside the undershirt/underwear.

7. The system according to claim 6, further comprising a software module for processing driver parameters, a position provided by the GPS and data of an in-board standard telemetry for comprehending the conditions, psychophysical reactions, under different conditions/situations which can occur during performed activities.

8. The system according to claim 3, wherein the system is configured to provide integrated detection of electrolysis and glycolysis to suitably determine food integrations required for the activities to be detected.

9. The system according to claim 3, wherein the perspiration parameter considers a phasic component associated to said skin galvanic response.

* * * * *